(12) United States Patent
Odaka et al.

(10) Patent No.: US 9,119,827 B2
(45) Date of Patent: Sep. 1, 2015

(54) OPHTHALMIC COMPOSITION

(75) Inventors: Akito Odaka, Tokyo (JP); Chieko Inoue, Tokyo (JP); Manabu Hattori, Tokyo (JP); Nobuhito Tabuchi, Tokyo (JP)

(73) Assignee: LION CORPORATION, Tokyo (JP)

( * ) Notice: Subject to any disclaimer, the term of this patent is extended or adjusted under 35 U.S.C. 154(b) by 0 days.

(21) Appl. No.: 13/381,604

(22) PCT Filed: Jun. 29, 2010

(86) PCT No.: PCT/JP2010/061005
§ 371 (c)(1),
(2), (4) Date: Dec. 29, 2011

(87) PCT Pub. No.: WO2011/001951
PCT Pub. Date: Jan. 6, 2011

(65) Prior Publication Data
US 2012/0108658 A1  May 3, 2012

(30) Foreign Application Priority Data

Jun. 30, 2009 (JP) ................................. 2009-154862

(51) Int. Cl.
| | | |
|---|---|---|
| *A61K 9/00* | (2006.01) | |
| *A61K 47/44* | (2006.01) | |
| *A61K 31/74* | (2006.01) | |
| *A61K 31/203* | (2006.01) | |
| *A61K 31/20* | (2006.01) | |
| *A61K 31/22* | (2006.01) | |
| *A61K 31/23* | (2006.01) | |
| *A61K 31/232* | (2006.01) | |

(52) U.S. Cl.
CPC ............ *A61K 31/203* (2013.01); *A61K 9/0048* (2013.01); *A61K 31/20* (2013.01); *A61K 31/22* (2013.01); *A61K 31/23* (2013.01); *A61K 31/232* (2013.01); *A61K 47/44* (2013.01)

(58) Field of Classification Search
USPC ................. 424/401, 78.04, 78.05; 514/725
See application file for complete search history.

(56) References Cited

U.S. PATENT DOCUMENTS

| | | | | |
|---|---|---|---|---|
| 5,951,971 | A * | 9/1999 | Kawashima et al. ...... 424/78.04 |
| 6,787,572 | B2 * | 9/2004 | Brancato et al. ............ 514/690 |
| 2004/0185068 | A1 * | 9/2004 | Yu et al. ..................... 424/401 |
| 2010/0120908 | A1 * | 5/2010 | Kimura et al. .............. 514/530 |
| 2010/0216741 | A1 | 8/2010 | Matsumura et al. |
| 2010/0249062 | A1 | 9/2010 | Matsumura et al. |

FOREIGN PATENT DOCUMENTS

| | | |
|---|---|---|
| JP | 2002-154989 A | 5/2002 |
| JP | 2006-117656 A | 5/2006 |
| JP | 2007-211007 A | 8/2007 |
| JP | 2008-094839 A | 4/2008 |
| JP | 2008-222638 A | 9/2008 |
| JP | 2008-308450 A | 12/2008 |
| WO | WO 2009/035033 A1 | 3/2009 |
| WO | WO 2009/041549 A1 | 4/2009 |

OTHER PUBLICATIONS

Usui et al. JP 2008-094839, Apr. 24, 2008, machine translation.*
International Search Report, PCT/JP2010/061005, Aug. 3, 2010.
Office Action issued Feb. 20, 2014, in Japanese Patent Application No. 2011-520919, with partial English translation.
Selek et al., "Evaluation of retinoic acid ophthalmic emulsion in dry eye," European Journal of Ophthalmology (2000), vol. 10, No. 2, pp. 121-127.
Waring et al., "Double-masked evaluation of a poloxamer artifical tear in keratoconjunctivitis sicca," Symposium on Ocular Therapy, vol. 11, John Wiley, New York, 1979, pp. 127-140.
"Vitamin A Oil," Commentary on the Japanese Pharmacopoeia, 16th Edition, C-3625, Horikawa-Shoten Ltd. (2011), with English translation.
Dictionary of Pharmaceutical Additives, Yakuji Nippo Limited (2007), p. 39.
Nikko Chemicals Catalog (2003), pp. 39-40.
Notification of Information Disclosure Statement issued Jun. 24, 2014, in Japanese Patent Application No. 2011-520919.
Shin Kesyouhingaku (2001), pp. 150-151.

* cited by examiner

*Primary Examiner* — Gina Justice
(74) *Attorney, Agent, or Firm* — Birch, Stewart, Kolasch & Birch, LLP

(57) ABSTRACT

Disclosed is an ophthalmic composition which is characterized by containing (A) a vitamin A, (B) a polyoxyethylene polyoxypropylene glycol, and (C) an oil component that is selected from the group consisting of castor oil, soybean oil, sesame oil, peanut oil, olive oil, almond oil, wheat germ oil, corn oil, rapeseed oil, sunflower oil, purified lanolin and gel hydrocarbon.

10 Claims, No Drawings

OPHTHALMIC COMPOSITION

TECHNICAL FIELD

This invention relates to an ophthalmic composition, which is formulated with vitamin A and has a dry eye treatment effect.

BACKGROUND ART

In recent years, dry-eye patients are increasing sharply in number in association with the indoor dryness ascribed to the spread of air conditioners, increasing operations of VDT such as personal computers, increasing number of contact lens users, and the diversity of changes in living and social environments. Dry eyes mean a state wherein the cornea and conjunctiva on the eyeball surface undergo a damage caused by the quantitative or qualitative abnormality of tear fluid. Tear fluid is constituted of three layers including an oil layer, an aqueous layer and a mucin layer. The tear fluid becomes unstabilized when the quantitative and qualitative balance of this three-layered structure is destroyed, so that the corneal disorder occurs, thereby bringing about dry eyes. In a dry-eye treatment, it is important to restore this three-layered structure of the oil layer, aqueous layer and mucin layer and to treat the corneal disorder.

PRIOR ART DOCUMENT

Patent Document

Patent Document 1: JP-A 2008-222638

SUMMARY OF THE INVENTION

Problems to be Solved by the Invention

Vitamin A is known as a substance essential for proliferation and differentiation of epithelial cells and has the action of promoting mucin production and the action of curing a corneal wound. Thus, vitamin A has been expected as a drug, which is useful for dry eye treatment and shows the effects on "restoration of the mucin layer of tear fluid" and "treatment of corneal and conjunctival disorders."

Further, vitamin A is lipophilic in nature, and if it is formulated in an ophthalmic composition in the form of an aqueous preparation, the oil layer and aqueous layer of tear fluid can also be supplemented. Accordingly, vitamin A-formulated ophthalmic compositions are enabled favorably as an eye drop, which is able to restore the three-layered structure of the oil layer, aqueous layer and mucin layer of tear fluid as being important for dry-eye treatment and is effective for corneal disorder treatment.

However, it is not clear that vitamin A alone is sufficient to supplement the oil layer of tear fluid, and a problem is involved in that if vitamin A is formulated in ophthalmic compositions in large amounts, side effects such as of eye irritation may be caused. In case where vitamin A is not sufficient for supplementing the oil layer of tear fluid, it may be considered to supplementarily formulate an oil ingredient. Such formulation essentially requires an increasing amount of surfactants, with the attendant problem that eye irritation is caused as will be described hereinafter.

In view of the circumstances set forth above, there has been demanded the development of ophthalmic compositions formulated with vitamin A wherein oil ingredients are formulated in amounts sufficient to supplement the oil layer of tear fluid and which are effective for dry eye treatment without causing eye irritation.

On the other hand, it is considered to use vitamin A as an oily eye drop or eye ointment. For supplementing an oil to tear fluid, it is most effective to administer an oily eye drop or eye ointment. However, when an oil component is administered directly to eyes, problems arise in that because of its inherent irritation and viscousness, "pain," blurred visions such as "blur," "blurred eyesight" and the like, and discomfort feelings such as "stickiness" develop. With contact lens users, another problem is involved in that an oil component is liable to cause the contact lenses to become cloudy or dirty.

An oil component can be solubilized or emulsified by means of surfactants. However, most of them are milky white preparations obtained by emulsification with a relatively small amount of surfactant. Although this type of preparation has a merit that eye irritation is low, there arises a problem in that when this preparation is stored over a long time, a difficulty is involved in keeping stability and homogeneity such as by separation of the oil component. In contrast, clear eye drops of the type wherein a large amount of surfactant is used for solubilizing an oil component are advantageous in that the oil component stably exists in the eye drop. Nevertheless, the surfactant is irritative against the cornea or conjunctiva and thus, a satisfactory effect on the prevention or amelioration of dry eye disorders has not necessarily be shown. Moreover, this problem becomes more pronounced when contact lenses are worn. In view of the foregoing, there has been demanded an ophthalmic composition that has an effect on the amelioration of dry eye disorders, is suppressed form eye irritation and has good appearance retention stability.

The invention has been made under such circumstances in the art and has for its object the provision of an ophthalmic composition that has an effect on the amelioration of dry eye symptoms, is suppressed form eye irritation and has good appearance retention stability.

Means for Solving the Problems

We have made intensive studies in order to achieve the above object and found that when (C) an oil ingredient such as a plant oil is formulated aside from (A) vitamin A, an oil layer in tear fluid can be well supplemented, thus leading to an improved effect on the amelioration of dry eyes and eye irritation is suppressed. Moreover, it has also been found that when (B) polyoxyethylene polyoxypropylene glycol is further formulated, an ophthalmic composition of the invention making use of the ingredients (A) and (C) in combination can be rendered clear thereby improving appearance retention stability and further improving the effect on the amelioration of dry eyes. Additionally, when (D) an antioxidant is further formulated, appearance retention stability can be further improved. When (E) a polyoxyethylene hardened castor oil or polyoxyethylene sorbitan fatty acid ester is further formulated, there can be obtained an ophthalmic composition, which is clear and has good appearance retention stability without causing eye irritation, thus arriving at completion of the invention.

Accordingly, the invention provides the following ophthalmic compositions.

[1]. An ophthalmic composition comprising (A) vitamin A, (B) polyoxyethylene polyoxypropylene glycol and (C) an oil ingredient selected from the group consisting of castor oil, soybean oil, sesame oil, peanut oil, olive oil, almond oil, wheat germ oil, corn oil, canola oil, sunflower oil, purified lanolin and a gelled hydrocarbon.

[2]. The ophthalmic composition of claim 1, wherein the ingredient (A) is retinol palmitate, retinol acetate or retinoic acid.
[3]. The ophthalmic composition of claim 1 or 2, wherein a content of the ingredient (B) is 0.1 to 20 W/V %.
[4]. The ophthalmic composition of claim 1, 2 or 3, wherein a content of the ingredient (C) is 0.01 to 5 W/V %.
[5]. The ophthalmic composition of in any one of claims 1 to 4, further comprising (D) an antioxidant.
[6]. The ophthalmic composition of claim 5, wherein the ingredient (D) is vitamin E or dibutylhydroxytoluene.
[7]. The ophthalmic composition of any one of claims 1 to 6, further comprising 0.001 to 0.5 W/V % of (E) a polyoxyethylene hardened castor oil and/or a polyoxyethylene sorbitan fatty acid ester.
[8]. The ophthalmic composition of claim 7, wherein a total content of the ingredients (B) and (E) is at least 1.1 W/V %.
[9]. The ophthalmic composition of any of claims 1 to 8, wherein no antiseptic is formulated.
[10]. The ophthalmic composition of any one of claims 1 to 9, wherein said composition is the ophthalmic composition for contact lens.

Advantageous Effect of the Invention

According to the invention, there can be provided an ophthalmic composition that has an amelioration effect of dry eye symptoms, is suppressed in eye irritation and has good appearance retention stability.

EMBODIMENT FOR CARRYING OUT THE INVENTION

The invention is now described in detail.
The ophthalmic composition of the invention comprises (A) vitamin A, (B) polyoxyethylene polyoxypropylene glycol and (C) an oil ingredient selected from the group consisting of castor oil, soybean oil, sesame oil, peanut oil, olive oil, almond oil, wheat germ oil, corn oil, canola oil, sunflower oil, purified lanolin and a gelled hydrocarbon.
(A) Vitamin A
Vitamin A includes vitamin A itself, vitamin A-containing mixtures such as vitamin A oil, vitamin A derivatives such as vitamin A fatty acid esters, and the like. These may be used singly or in appropriate combination of two or more. More particularly, mention is made of retinol palmitate, retinol acetate, retinol, retinoic acid, retinoide and the like. Of these, retinol palmitate, retinol acetate and retinoic acid are preferred. Retinol palmitate is commercially sold usually as having 1,000,000 to 1,800,000 international units (hereinafter abbreviated as units or I.U.), and specific mention is made of "retinol palmitate" (1,700,000 I.U./g), made by Roche Vitamin Japan K.K.).
The amount of the ingredient (A) is preferably 50,000 to 500,000 units/100 mL, more preferably 50,000 to 300,000 units/100 mL, and further preferably 100,000 to 200,000 units/100 mL in the ophthalmic composition. When expressed by W (weight)/V (volume) % (g/100 mL), the amount is preferably 0.03 to 0.3 W/V %, more preferably 0.03 to 0.18 W/V % and further preferably 0.06 to 0.12 W/V % although depending on the units of vitamin A being formulated. Vitamin A has a corneal/conjunctival damage treatment effect and amelioration effects on dry eye, tired eye and bleary eye conditions. If the amount is less than 50,000 units/100 mL, there is concern that the corneal/conjunctival damage treatment effect becomes unsatisfactory and the dry eye treatment effect also becomes unsatisfactory. Over 500,000 units/100 mL, there is concern that problems of side effects may develop.
(B) Polyoxyethylene Polyoxypropylene Glycol
Polyoxyethylene polyoxypropylene glycol is not particularly limited in type and those described in Japanese Pharmaceutical Excipients (JPE) may be used. The average degree of polymerization of ethylene oxide is preferably at 4 to 200, more preferably at 20 to 200 and the average degree of polymerization of propylene oxide is preferably at 5 to 100, more preferably at 20 to 70, and either a block copolymer or a random polymer may be used. The ingredients (B) may be used singly or in combination of two or more. When a specific type of surfactant is used as the ingredient (B), an ophthalmic composition of the invention making use of the ingredients (A) and (C) in combination can be rendered clear, enabling appearance retention stability to be improved and an amelioration effect on dry eye symptoms to be more shown. In addition, if the ingredient (B) is formulated in large amounts, eye irritation is unlikely to occur.

In particular, examples of polyoxyethylene polyoxypropylene glycol include polyoxyethylene (200) polyoxypropylene (70) glycol such as Lutrol F127 (made by BASF), Uniloob 70DP-950B (made by NFO Corporation) or the like, polyoxyethylene (120) polyoxypropylene (40) glycol (Pluronic F-87), polyoxyethylene (160) polyoxypropylene (30) glycol ((Pluronic F-68, otherwise known as Poloxamer 188) such as Plonon #188P (made by NFO corporation) and the like, polyoxyethylene (42) polyoxypropylene (67) glycol ((Pluronic P123, otherwise known as Poloxamer 403), polyoxyethylene (54) polyoxypropylene (39) glycol (Pluronic P85) such as Plonon #235P (made by NFO corporation) and the like, polyoxyethylene (20) polyoxypropylene (20) glycol (Pluronic L-44), Tetronic and the like. Of these, polyoxyethylene (200) polyoxypropylene (70) glycol, polyoxyethylene (160) polyoxypropylene (30) glycol, and polyoxyethylene (54) polyoxypropylene (39) glycol are preferred.

The amount of the ingredient (B) in the ophthalmic composition is preferably 0.1 to 20 W/V %, more preferably 0.2 to 15 W/V %, much more preferably 0.5 to 10 W/V %, further preferably 1.1 to 10 W/V % and most preferably 3 to 10 W/V %. If the amount is less than 0.1 W/V %, there is concern that a difficulty is involved in the solubilization of an oil ingredient. Over 20 W/V %, there is concern that eye irritation may develop. Nevertheless, the formulation of the ingredient (B) in large amounts is unlikely to cause eye irritation. In case where the ingredient (B) is formulated singly as a solubilizing agent in an amount of not less than 0.4 W/V %, the solubilization of an oil ingredient becomes easy.
(C) Oil Ingredient
An oil ingredient is selected from the group consisting of castor oil, soybean oil, sesame oil, peanut oil, olive oil, almond oil, wheat germ oil, corn oil, canola oil, sunflower oil, purified lanolin and a gelled hydrocarbon, which may be used singly or in combination of two or more. Of these, castor oil, sesame oil, olive oil, soybean oil, and peanut oil are more preferred, castor oil, sesame oil, soybean oil, and peanut oil are much more preferred and castor oil, sesame oil and soybean oil are further preferred. When using vitamin (A) and the oil ingredient (C) are used in combination, the amelioration effect on dry eye symptoms is improved.

From the standpoints of the amelioration of dry eye symptoms and appearance stability, the amount of the ingredient (C) is preferably 0.01 to 5 W/V %, more preferably at 0.05 to 3 W/V % in the ophthalmic composition. If the amount is less than 0.01 W/V %, it would be difficult to obtain a good feeling of use. Over 5 W/V %, there would be some case where a clear eye drop cannot be obtained.

(D) Antioxidant

From the viewpoints of improving storage stability and appearance retention stability of vitamin A, it is preferred to formula an antioxidant. Examples of antioxidant include vitamin E and derivatives thereof such as d-α-tocopherol, d-β-tocopherol, d-γ-tocopherol, d-δ-tocopherol, dl-α-tocopherol, d-α-tocopherol acetate, dl-α-tocopherol acetate, dl-δ-tocopherol acetate, dl-γ-tocopherol acetate, dl-δ-tocopherol acetate, dl-α-tocopherol nicotinate and the like, lipophilic antioxidants such as dibutylhydroxytoluene, butylhydroxy anisole and the like, and water-soluble antioxidants such as vitamin C, hydroquinone, cysteine, glutathione and the like. These may be used singly or in combination of two or more. Of these, lipophilic antioxidants such as vitamin E are preferred, d-α-tocopherol acetate and dibutylhydroxytoluene are more preferred, and d-α-tocopherol acetate is further preferred.

The amount of the ingredient (D) is preferably 0.001 to 0.5 W/V %, more preferably 0.005 to 0.3 W/V % in the ophthalmic composition.

(E) Polyoxyethylene Hardened Castor Oil and/or Polyoxyethylene Sorbitan Fatty Acid Ester From the standpoint of appearance retention stability, it is preferred to formulate a polyoxyethylene hardened castor oil and/or polyoxyethylene sorbitan fatty acid ester in the ophthalmic composition of the invention. Examples of polyoxyethylene hardened castor oil include polyoxyethylene hardened castor oil (E.O.) 5, polyoxyethylene hardened castor oil 10, polyoxyethylene hardened castor oil 20, polyoxyethylene hardened castor oil 40, polyoxyethylene hardened castor oil 50, polyoxyethylene hardened castor oil 60, polyoxyethylene hardened castor oil 100 and the like. As a polyoxyethylene sorbitan fatty acid ester, mention is made of polyoxyethylene (20) sorbitan monolaurate (Polysorbate 20), polyoxyethylene (20) sorbitan monooleate (Polysorbate 80), polyoxyethylene sorbitan monostearate (Polysorbate 60), polyoxyethylene sorbitan tristearate (Polysorbate 65) and the like. These may be used singly or in appropriate combination of two or more. Of these, Polysorbate 80 and polyoxyethylene hardened castor oil 60 are preferred.

The ingredient (E) can be formulated within a range not causing eye irritation. The amount is preferably 0.001 to 0.5 W/V %, more preferably at 0.01 to 0.4 W/V % and further preferably at 0.05 to 0.3 W/V % in the ophthalmic composition.

The total amount of the ingredients (B) and (E) is preferably at least 1.1 W/V %, more preferably at least 2 W/V %, from the standpoint of improving appearance retention stability. As stated hereinabove, the ingredient (E) is preferably at not larger than 0.5 W/V % in view of improving dry eyes and preventing eye irritation.

The ophthalmic composition of the invention may be further formulated, aside from the above-stated ingredients, a variety of ingredients formulated in ophthalmic compositions within ranges not impeding the effects of the invention. These ingredients include polyhydric alcohols, surfactants other than the ingredients (B) and (E), buffering agents, thickening agents, sugars, pH adjusters, antiseptics, tonicity agents, stabilizing agents, cooling agents, drugs, water and the like. These may be used singly or in combination of two or more types, and appropriate amounts may be formulated.

Examples of polyhydric alcohol include glycerine, propylene glycol, butylene glycol, polyethylene glycol and the like. The amount of the polyhydric alcohol is preferably 0.01 to 5 W/V %, more preferably at 0.05 to 3 W/V % in the ophthalmic composition.

Surfactants other than the ingredients (B) and (E) may be used in combination therewith and include, for example, glycine-based amphoteric surfactants such as alkyldiaminoethylglycines, and cationic surfactants such as alkyl quaternary ammonium salts (particularly, benzalkonium chloride, benzethonium chloride and the like). The amount of these surfactants in the ophthalmic composition is preferably at 0.0001 to 10 W/V %, more preferably at 0.005 to 5 W/V %.

Examples of buffering agent include boric acid or its salt (borax or the like), citric acid or its salt (sodium citrate or the like), phosphoric acid or its salt (sodium monohydrogen phosphate or the like), tartaric acid or its salt (sodium tartarate or the like), gluconic acid or its salt (sodium gluconate or the like), acetic acid or its salt (sodium acetate or the like), a variety of amino acids (epsilon-aminocaproic acid, potassium aspartate, aminoethylsulfonic acid, glutamic acid, sodium glutamate and the like), and trometamol, etc. Of these, trometamol is preferred from the viewpoint of low irritation and the antiseptic effect of composition. Moreover, when boric acid and borax are used in combination, a high antiseptic effect can be obtained. It will be noted that in the practice of the invention, when boric acid, trometamol and citric acid or its salt are formulated, the stability of vitamin A is further improved. The amount of the buffering agent in the ophthalmic composition is preferably at 0.001 to 10 W/V %, more preferably at 0.01 to 5 W/V %.

Examples of thickening agent include polyvinyl pyrrolidone, hydroxyethylcellulose, hydroxypropyl methylcellulose, methylcellulose, polyvinyl alcohol, sodium hyarulonate, sodium chondroitin sulfate, polyacrylic acid, carboxyvinyl polymer and the like. The formulation of these ingredients permits high retention, thereby leading to a more improved corneal/conjunctival damage treatment effect. The amount of the thickening agent in the ophthalmic composition, for example, preferably at 0.001 to 10 W/V %, more preferably at 0.001 to 5 W/V % and further preferably at 0.01 to 3 W/V %.

Examples of sugar include glucose, cyclodextrin, xylitol, sorbitol, mannitol and the like. It will be noted that these may be any of a d isomer, an l isomer or a dl isomer. The amount of sugar is, for example, at 0.001 to 10 W/V %, preferably at 0.005 to 5 W/V % and further preferably at 0.01 to 3 W/V %.

It is preferred to use, as a pH adjuster, an inorganic acid or inorganic alkali. For example, (diluted) hydrochloric acid can be mentioned as an inorganic acid. As an inorganic alkali, mention is made of sodium hydroxide, potassium hydroxide, sodium carbonate, sodium hydrogen carbonate and the like. Of these, hydrochloric acid and sodium hydroxide are preferred. The pH (20° C.) of the ophthalmic composition of the invention is preferably at 4.0 to 9.0, more preferably at 5.0 to 8.0 and further preferably at 6.0 to 8.0. It will be noted that in the practice of the invention, the measurement of pH is carried out using a pH osmometer (HOSM-1, made by DKK-To a Corporation) at 20° C. The amount of the pH adjuster in the ophthalmic composition, for example, at 0.00001 to 10 W/V %, preferably at 0.0001 to 5 W/V % and further preferably at 0.001 to 3 W/V %.

Examples of antiseptic include benzalkonium chloride, benzethonium chloride, sorbic acid or a salt thereof, paraoxybenzoic acid esters (such as methylparaben, ethylparaben, propylparaben and the like), chlorhexidine gluconate, thimerosal, phenyl ethyl alcohol, alkyldiaminoethylglycine hydrochloride, polyhexanide hydrochloride, polydronium chloride and the like. Although the antiseptic may be formulated within a range not impeding the effect of the invention, it is preferred that the ophthalmic composition of the invention should be complexly free of an antiseptic, in which no antiseptic is contained, from the standpoint of eye irritation.

From the viewpoint of dry eye improvement in the practice of the invention, the amount of a cationic surfactant selected from benzalkonium chloride and benzethonium chloride (part of which is a cationic antiseptic) and a hydrophobic antiseptic selected from paraoxybenzoic acid esters (methylparaben, ethylparaben, propylparaben and the like) and chlorobutanol is preferably at not larger than 0.004 W/V %, more preferably at not larger than 0.003 W/V % and further preferably in such a way that these are not contained with no antiseptic. Although there is not known a mechanism as to how to block the corneal/conjunctival damage treatment effect. This may be considered in the following way. Polyoxyethylene polyoxypropylene glycol (B) forms micelles wrapping vitamin A with the EO chain kept outside and the PO chain kept inside. This micelle is adsorbed on the cornea surface and vitamin A is absorbed inside the cornea. It is considered that cationic surfactants have high surface activity or hydrophobic antiseptics are high in hydrophobicity, so that the surface state of the micelle is changed thereby blocking the adsorption of vitamin A on the cornea. Eventually, the corneal/conjunctival damage treatment effect and dry eye improvement are inhibited. On the other hand, those having high hydrophilicity such as sorbic acid or its salt do not influence the state of the micelle surface and do not block the absorption-expediting effect of vitamin A. It will be noted that the above ingredient serves as a part of antiseptic and the antiseptic power in case where no antiseptic is formulated can be attained by formulation of one or more, preferably two or more, of sodium edetate, boric acid and trometamol in combination. If there is used a unit dose container or a filtered container, no antiseptic formulation is possible.

Examples of tonicity agent include sodium chloride, potassium chloride and the like. The amount of the tonicity agent is, for example, at 0.001 to 5 W/V %, preferably at 0.01 to 3 W/V % and further preferably at 0.1 to 2 W/V %.

Examples of stabilizing agent include sodium edetate, cyclodextrin, sulfites, dibutylhydroxytoluene and the like. It will be noted that in the invention, the formulation of the stabilizing agent leads to improved stability of vitamin A. The amount of the stabilizing agent is, for example, at 0.001 to 5 W/V %, preferably at 0.01 to 3 W/V % and further preferably at 0.1 to 2 W/V %.

Examples of cooling agent include menthol, camphor, borneol, geraniol, cineol, linalool and the like. The amount of the cooling agent as a total amount of compounds in the ophthalmic composition is preferably at 0.0001 to 5 W/V %, preferably at 0.001 to 2 W/V %, further preferably at 0.005 to 1 W/V % and most preferably at 0.007 to 0.8 W/V %.

A drug (pharmaceutically effective ingredient), there may be appropriately formulated, for example, a decongestant (e.g. naphazoline hydrochloride, tetrahydrozoline hydrochloride, phenylephrine hydrochloride, epinephrine, ephedrine hydrochloride, dl-methylephedrine hydrochloride, tetrahydrozoline nitrate, naphazoline nitrate or the like), an antiphlogistic/astringent agent (e.g. neostigmine methylsulfate, e-aminocaproic acid, allantoin, berberine chloride, zinc sulfate, zinc lactate, lysozyme chloride, dipotassium glycyrrhizinate, ammonium glycyrrhizinate, glycyrrhetinic acid, methyl salicylate, tranexamic acid, azulene sodium sulfonate or the like), an antihistamine agent (e.g. iproheptine hydrochloride, diphenhydramine hydrochloride, diphenhydramine, isothipendyl hydrochloride, chlorpheniramine maleate or the like), an anti-allergic agent (e.g. sodium cromoglycate or the like), a water-soluble vitamin (activated vitamin $B_2$, vitamin $B_6$, vitamin $B_{12}$ or the like), an amino acid (e.g. potassium L-aspartate, magnesium L-aspartate, aminoethylsulfonic acid, sodium chondroitin sulfate, glutathione or the like), a sulfa drug or bactericide (e.g. sulfur, isopropylmethylphenol, hinokitiol or the like), a regional anesthetic (e.g. lidocaine, lidocaine hydrochloride, procaine hydrochloride, dibucaine hydrochloride or the like), and a mydriatic drug (e.g. tropicamide or the like).

The amount of these ingredients in the ophthalmic composition may be appropriately selected depending on the types of preparations and the types of drugs and are known in this field of technology. For instance, the amount can be appropriately chosen from a range of 0.0001 to 30 W/V %, preferably from 0.001 to 10 W/V %, in the ophthalmic composition. More particularly, the amounts of the respective ingredients in the ophthalmic composition are just as follows.

With a decongestant, the amount is, for example, 0.0001 to 0.5 W/V %, preferably 0.0005 to 0.3 W/V % and more preferably 0.001 to 0.1 W/V %. With an antiphlogistic/astringent agent, the amount is, for example, 0.0001 to 10 W/V %, preferably 0.0001 to 5 W/V %. With an antihistamine agent, its amount is, for example, 0.0001 to 10 W/V %, preferably 0.001 to 5 W/V %. With a water-soluble vitamin, its amount is, for example, 0.0001 to 1 W/V %, preferably 0.0001 to 0.5 W/V %. With an amino acid, the amount is, for example, 0.0001 to 10 W/V %, preferably 0.001 to 3 W/V %. With a sulfur drug or bactericide, the amount is, for example, 0.00001 to 10 W/V %, preferably 0.0001 to 10 W/V %. With a regional anesthetic, the amount is, for example, 0.001 to 1 W/V %, preferably 0.01 to 1 W/V %.

The ophthalmic composition of the invention may be used as it is in liquid form, or may be prepared as a suspension, a gelling agent or the like. As an ophthalmic composition, mention may be made of eye drops, eye washes and the like and those for contact lens are suited. It will be noted that the term "for contact lens" means ones that are used upon wearing contact lenses. More particularly, mention is made of eye drops (including those eye drops for contact lens, which may be instilled when wearing contact lenses), and eye washes (including eye washes, which may be used for eye washing when wearing contact lenses), of which eye drops for contact lenses are preferred. Contact lenses are not critical in type, for which mention is made of hard contact lenses, oxygen permeable hard contact lenses, soft contact lenses, disposable contact lenses, silicone-hydrogel contact lenses and the like.

Since vitamin A is formulated at high concentrations in the practice of the invention, the composition is suited as an ophthalmic composition for corneal damage treatment or a dry eye remedy. It will be noted that the "dry eye" means a state of the cornea and conjunctiva on the surface of the eyeball, which undergo a disorder associated with the qualitative or quantitative abnormality of tear fluid. The tear fluid is constituted of three layers including an oil layer, an aqueous layer and a mucin layer and when the qualitative and quantitative balance of this three-layered structure is destroyed, the tear fluid becomes unstable, so that the cornea is damaged, thereby bringing about eye dryness. For dry eye treatment, it is important to restore the three-layered structure of the oil layer, aqueous layer and mucin layer of the tear fluid and subject to corneal disorder treatment. Contact lens users are liable to undergo dry eyes. Therefore, the ophthalmic composition of the invention is suitable as eye drops for contact lenses, eye washes to be used after removal of contact lenses, contact lens-wearing solutions, solutions to be used for removal of contact lenses and the like. When used as a dry eye remedy, the composition is able to show a better effect when it is instilled into the eyes in an amount of 30 to 60 μl per time and three to six times per day.

According to the invention, the ophthalmic composition can be made clear. It is to be noted that the term "clear" means to be transparent without turbidity.

The ophthalmic composition of the invention is liquid in nature and when used as an eye drop, its viscosity is preferably at 1 to 50 mPa·s, more preferably at 1 to 20 mPa·s and further preferably at 1 to 5 mPa·s. It will be noted that the viscosity is measured at 20° C. by use of an E-type viscometer (VISCONIC ELD-R, made by Tokyo Keiki Inc.).

The ophthalmic composition of the invention is not critical with respect to its preparation method. For instance, the composition can be obtained by solubilizing vitamin A in purified water with the aid of polyoxyethylene polyoxypropylene glycol, followed by adding other formulation ingredients and adjusting a pH thereof. Thereafter, the composition can be aseptically filled in an appropriate container, for example, a polyethylene terephthalate container.

EXAMPLES

Examples and Comparative Examples are now shown to particularly illustrate the invention, which should not be construed as limited to the following Examples. It will be noted that amounts in tables mean those of pure ingredients.

Examples 1 to 44, Comparative Examples 1 to 4

Ophthalmic compositions (eye drops) having formulations indicated in Tables 1 to 8 were prepared. Vitamin A, polyoxyethylene polyoxypropylene glycol and oil ingredients (an antioxidant, as required) were preliminarily dissolved at 85° C. This preliminarily dissolved matter was solubilized in purified water, heated to 85° C. After cooling, water-soluble ingredients were added. The resulting ophthalmic compositions (eye drops) were evaluated in the following way. The results are also shown in the tables. The pH (20° C.) of the ophthalmic composition was measured by use of a pH osmometer (HOSM-1, made by DKK-To a Corporation) with the results shown in the tables. It should be noted that all the ophthalmic compositions of the examples were clear.

<Appearance Stability>

20 mL of an ophthalmic compositions was filled in a glass ampule (for 20 mL usage) and a change in appearance seven days after storage at 70° C. was observed and evaluated according to the following standards.

<Evaluation Standards>
  5: Solution was clear with little discoloration.
  4: Although solution was clear, it underwent a very slight degree of discoloration.
  3: Although solution was clear, it underwent a slight degree of discoloration.
  2: Solution was not clear.
  1: Solution was separated or precipitated.

<Dry Eye Improvement 1>

Patients complained of dry eye symptoms (severity level 1: see The Ocular Surface Vol. 5, No. 2, 2007) was instilled with 50 μl of an ophthalmic composition (three times each at intervals of two hours), followed by evaluating a degree of dry eye improvement 30 minutes after the third cycle of the instillation according to the following evaluation standards.

<Evaluation Standards>
  5: Remarkably improved
  4: Improved
  3: Slightly improved
  2: Yes and no
  1: Not improved <Dry Eye Improvement 2>

Patients (three persons) complained of dry eye symptoms (severity level 4) was instilled with 50 μL of an ophthalmic composition (three times each at intervals of two hours), followed by evaluating a degree of dry eye improvement (eye dryness) 30 minutes after the third cycle of the instillation according to the following evaluation standards. The results are shown in terms of average value (rounded off to the nearest whole number).

<Evaluation Standards>
  7: Extremely improved
  6: Much improved
  5: Fairly improved
  4: Improved
  3: Slightly improved
  2: Yes or no
  1: Not improved <Eye Irritation>

5 mL of an ophthalmic composition was taken in a cup for eye washing and used for eye washing for 30 seconds. Eye irritation felt during the eye washing was evaluated according to the following standards. It will be noted that eye washing was made in a state of lying on one's back under such conditions that the eye washing solution did not drop out from the eye washing cup and blink was made at intervals of once every five seconds so that the eye washing solution entirely covered the eye surface.

<Evaluation Standards>
  5: No irritation felt
  4: Yes or no
  3: Irritation felt slightly
  2: Irritation felt appreciably
  1: Irritation felt considerably

TABLE 1

| | Formulation (W/V %) | Example | | | | Comparative Example | | | |
|---|---|---|---|---|---|---|---|---|---|
| | | 1 | 2 | 3 | 4 | 1 | 2 | 3 | 4 |
| (A) | Retinol palmitate | 50,000 units | 50,000 units | 50,000 units | 50,000 units | 50,000 units | — | — | 50,000 units |
| (B) | Polyoxyethylene (200) polyoxypropylene glycol (70) *1 | 3 | 3 | 3 | 3 | — | 3 | 3 | 3 |
| (C) | Castor oil | 0.5 | 0.5 | — | — | 0.5 | 0.5 | — | — |
| | Sesame oil | — | — | 0.2 | 0.2 | — | — | — | — |

TABLE 1-continued

| | Formulation | Example | | | | Comparative Example | | | |
|---|---|---|---|---|---|---|---|---|---|
| | (W/V %) | 1 | 2 | 3 | 4 | 1 | 2 | 3 | 4 |
| (D) | d-α-Tocopherol acetate | — | 0.05 | — | 0.05 | — | — | — | — |
| (E) | Polyoxyethylene hardened castor oil 60 | — | 0.1 | — | — | 3 | — | — | — |
| | Polysorbate 80 | — | — | — | — | — | — | — | — |
| Others | Sodium chloride | 0.9 | 0.9 | 0.9 | 0.9 | 0.9 | 0.9 | 0.9 | 0.9 |
| | Diluted hydrochloric acid/ sodium hydroxide (pH = 7.2) | | | | Appropriate amount | | | | |
| | Purified water | | | | Balance | | | | |
| Total | | | | | 100 mL | | | | |
| (B) + (E) | | 3 | 3.1 | 3 | 3 | 3 | 3 | 3 | 3 |
| Appearance stability | | 3 | 5 | 3 | 4 | 3 | 3 | 4 | 4 |
| Dry eye improvement 1 | | 5 | 5 | 5 | 5 | 3 | 2 | 1 | 4 |
| Dry eye improvement 2 | | 7 | 7 | 7 | 7 | 4 | 2 | 1 | 5 |
| Eye irritation | | 5 | 5 | 5 | 5 | 1 | 5 | 4 | 5 |

TABLE 2

| | Formulation | Example | | | | | |
|---|---|---|---|---|---|---|---|
| | (W/V %) | 5 | 6 | 7 | 8 | 9 | 10 |
| (A) | Retinol palmitate | 50,000 units | 50,000 units | 50,000 units | 50,000 units | 50,000 units | 50,000 units |
| (B) | Polyoxyethylene (200) polyoxypropylene glycol (70) *1 | 5 | 5 | 5 | 5 | 5 | 5 |
| (C) | Castor oil | 0.05 | — | — | — | — | — |
| | Soybean oil | — | 0.05 | — | — | — | — |
| | Sesame oil | — | — | 0.05 | — | — | — |
| | Peanut oil | — | — | — | 0.05 | — | — |
| | Olive oil | — | — | — | — | 0.05 | — |
| | Almond oil | — | — | — | — | — | 0.05 |
| | Wheat germ oil | — | — | — | — | — | — |
| | Corn oil | — | — | — | — | — | — |
| | Canola oil | — | — | — | — | — | — |
| | Sunflower oil | — | — | — | — | — | — |
| | Purified lanolin | — | — | — | — | — | — |
| | Gelled hydrocarbon | — | — | — | — | — | — |
| Others | Sodium chloride | 0.9 | 0.9 | 0.9 | 0.9 | 0.9 | 0.9 |
| | Diluted hydrochloric acid/ sodium hydroxide (pH = 7) | | | Appropriate amount | | | |
| | Purified water | | | Balance | | | |
| Total | | | | 100 mL | | | |
| (B) + (E) | | 5 | 5 | 5 | 5 | 5 | 5 |
| Appearance stability | | 3 | 3 | 3 | 3 | 3 | 3 |
| Dry eye improvement 1 | | 5 | 5 | 5 | 4 | 4 | 4 |
| Dry eye improvement 2 | | 7 | 7 | 7 | 6 | 6 | 6 |
| Eye irritation | | 5 | 5 | 5 | 5 | 5 | 5 |

TABLE 3

| | Formulation | Example | | | | | |
|---|---|---|---|---|---|---|---|
| | (W/V %) | 11 | 12 | 13 | 14 | 15 | 16 |
| (A) | Retinol palmitate | 50,000 units | 50,000 units | 50,000 units | 50,000 units | 50,000 units | 50,000 units |
| (B) | Polyoxyethylene (200) polyoxypropylene glycol (70) *1 | 5 | 5 | 5 | 5 | 5 | 5 |
| (C) | Castor oil | — | — | — | — | — | — |
| | Soybean oil | — | — | — | — | — | — |
| | Sesame oil | — | — | — | — | — | — |
| | Peanut oil | — | — | — | — | — | — |
| | Olive oil | — | — | — | — | — | — |
| | Almond oil | — | — | — | — | — | — |
| | Wheat germ oil | 0.05 | — | — | — | — | — |
| | Corn oil | — | 0.05 | — | — | — | — |
| | Canola oil | — | — | 0.05 | — | — | — |

TABLE 3-continued

| Formulation | | Example | | | | | |
|---|---|---|---|---|---|---|---|
| (W/V %) | | 11 | 12 | 13 | 14 | 15 | 16 |
| | Sunflower oil | — | — | — | 0.05 | — | — |
| | Purified lanolin | — | — | — | — | 0.05 | — |
| | Gelled hydrocarbon | — | — | — | — | — | 0.05 |
| Others | Sodium chloride | 0.9 | 0.9 | 0.9 | 0.9 | 0.9 | 0.9 |
| | Diluted hydrochloric acid/ sodium hydroxide (pH = 7) | Appropriate amount | | | | | |
| | Purified water | Balance | | | | | |
| Total | | 100 mL | | | | | |
| (B) + (E) | | 5 | 5 | 5 | 5 | 5 | 5 |
| Appearance stability | | 3 | 3 | 3 | 3 | 3 | 3 |
| Dry eye improvement 1 | | 4 | 4 | 4 | 4 | 4 | 4 |
| Dry eye improvement 2 | | 6 | 5 | 6 | 6 | 6 | 5 |
| Eye irritation | | 5 | 5 | 5 | 5 | 5 | 5 |

TABLE 4

| Formulation | | Example | | | | | | | |
|---|---|---|---|---|---|---|---|---|---|
| (W/V %) | | 17 | 18 | 19 | 20 | 21 | 22 | 23 | 24 |
| (A) | Retinol palmitate | 50,000 units | 50,000 units | 50,000 units | 50,000 units | 50,000 units | 100,000 units | 200,000 units | 500,000 units |
| (B) | Polyoxyethylene (200) polyoxypropylene glycol (70) *1 | 5 | 5 | 5 | 5 | 5 | 5 | 5 | 5 |
| (C) | Castor oil | 0.01 | 0.1 | 0.5 | 3.0 | 5.0 | 0.05 | 0.05 | 0.05 |
| Others | Sodium chloride | 0.9 | 0.9 | 0.9 | 0.9 | 0.9 | 0.9 | 0.9 | 0.9 |
| | Diluted hydrochloric acid/ sodium hydroxide (pH = 7) | Appropriate amount | | | | | | | |
| | Purified water | Balance | | | | | | | |
| Total | | 100 mL | | | | | | | |
| (B) + (E) | | 5 | 5 | 5 | 5 | 5 | 5 | 5 | 5 |
| Appearance stability | | 4 | 3 | 3 | 3 | 2 | 3 | 3 | 3 |
| Dry eye improvement 1 | | 4 | 5 | 5 | 5 | 5 | 5 | 5 | 5 |
| Dry eye improvement 2 | | 5 | 7 | 7 | 7 | 7 | 7 | 7 | 7 |
| Eye irritation | | 5 | 5 | 5 | 5 | 5 | 5 | 5 | 5 |

TABLE 5

| Formulation | | Example | | | | | |
|---|---|---|---|---|---|---|---|
| (W/V %) | | 25 | 26 | 27 | 28 | 29 | 30 |
| (A) | Retinol palmitate | 50,000 units | 50,000 units | 100,000 units | 150,000 units | 200,000 units | 200,000 units |
| (B) | Polyoxyethylene (200) polyoxypropylene glycol (70) *1 | 0.3 | 1.1 | 5 | 5 | 5 | 15 |
| (C) | Castor oil | 0.05 | — | 1 | — | — | 5 |
| | Soybean oil | — | 0.1 | — | — | — | — |
| | Olive oil | — | — | — | — | 0.01 | — |
| | Almond oil | — | — | — | 1 | — | — |
| (D) | d-α-Tocopherol acetate | — | 0.005 | 0.1 | 0.05 | 0.05 | 0.5 |
| | Dibutylhydroxytoluene | 0.001 | 0.005 | 0.005 | 0.005 | 0.005 | 0.005 |
| (E) | Polyoxyethylene hardened castor oil 60 | 0.5 | — | 0.5 | — | 0.3 | — |
| | Polyoxyethylene hardened castor oil 40 | — | 0.001 | — | 0.05 | — | 0.2 |
| | Polysorbate 80 | 0.3 | — | — | — | — | — |
| Others | Hydroxyethyl cellulose | 0.01 | — | — | — | — | — |
| | Sodium hyaluronate | — | — | — | — | — | 0.05 |
| | Sodium chondroitin sulfate | — | 0.1 | — | — | — | — |
| | Potassium L-aspartate | 1 | 1 | — | — | — | — |
| | Trometamol | 0.005 | 0.005 | — | 0.005 | — | 0.005 |
| | Boric acid | 1.5 | 1.5 | 1.3 | 1.5 | 1.5 | 1.5 |
| | Borax | — | — | 0.2 | — | 0.2 | — |
| | 1-Menthol | 0.005 | — | — | 0.005 | — | — |
| | dl-Camphor | 0.002 | — | — | 0.002 | — | — |
| | d-Borneol | 0.003 | — | — | 0.003 | — | — |

TABLE 5-continued

| Formulation | | Example | | | | | |
|---|---|---|---|---|---|---|---|
| (W/V %) | | 25 | 26 | 27 | 28 | 29 | 30 |
| | Sodium edetate | 0.1 | 0.1 | 0.1 | 0.1 | 0.1 | 0.1 |
| | Potassium sorbate | 0.1 | | | | 0.1 | |
| | Sodium chloride | 0.4 | 0.2 | 0.7 | 0.4 | 0.7 | 0.5 |
| | Diluted hydrochloric acid/ sodium hydroxide (pH = 7) | | | Appropriate amount | | | |
| | Purified water | | | Balance | | | |
| Total | | | | 100 mL | | | |
| (B) + (E) | | 1.1 | 1.101 | 5.5 | 5.05 | 5.3 | 15.2 |
| Appearance stability | | 5 | 5 | 5 | 5 | 5 | 5 |
| Dry eye improvement 1 | | 5 | 5 | 5 | 5 | 5 | 5 |
| Dry eye improvement 2 | | 7 | 7 | 7 | 7 | 7 | 7 |
| Eye irritation | | 4 | 5 | 5 | 5 | 5 | 5 |

TABLE 6

| Formulation | | Example | | |
|---|---|---|---|---|
| (W/V %) | | 31 | 32 | 33 |
| (A) | Retinol palmitate | 200,000 units | 200,000 units | 500,000 units |
| (B) | Polyoxyethylene (200) polyoxypropylene glycol (70) *1 | 5 | 5 | 20 |
| (C) | Castor oil | — | — | 2 |
| | Wheat germ oil | 0.1 | — | — |
| | Canola oil | — | 1 | — |
| (D) | d-α-Tocopherol acetate | 0.05 | 0.3 | 0.5 |
| | Dibutylhydroxytoluene | 0.005 | 0.005 | 0.005 |
| (E) | Polyoxyethylene hardened castor oil 60 | 0.2 | 0.01 | 0.001 |
| | Polysorbate 80 | 0.2 | — | — |
| Others | Sodium hyaluronate | 0.02 | — | — |
| | Polyvinylpyrrolidone | — | 0.1 | — |
| | Trometamol | 0.005 | 0.005 | 0.005 |
| | Boric acid | 1.5 | 1.5 | 1.5 |
| | Sodium edetate | 0.1 | 0.1 | 0.1 |
| | Sodium chloride | 0.9 | 0.9 | 0.9 |
| | Diluted hydrochloric acid/ sodium hydroxide (pH = 7) | | Appropriate amount | |
| | Purified water | | Balance | |
| Total | | | 100 mL | |
| (B) + (E) | | 5.4 | 5.01 | 20.001 |
| Appearance stability | | 5 | 5 | 5 |
| Dry eye improvement 1 | | 5 | 5 | 5 |
| Dry eye improvement 2 | | 7 | 7 | 7 |
| Eye irritation | | 5 | 5 | 5 |

TABLE 7

| Formulation | | Example | | | | |
|---|---|---|---|---|---|---|
| (W/V %) | | 34 | 35 | 36 | 37 | 38 |
| (A) | Retinol palmitate | 50,000 units | 50,000 units | 70,000 units | 150,000 units | 200,000 units |
| (B) | Polyoxyethylene (200) polyoxypropylene glycol (70) *1 | 0.1 | 0.5 | 1.1 | 3 | 5 |
| (C) | Castor oil | — | 0.3 | 0.5 | — | 1 |
| | Sesame oil | 0.5 | — | — | — | — |
| | Purified lanolin | — | — | — | 0.2 | — |
| (D) | d-α-Tocopherol acetate | 0.01 | 0.05 | 0.05 | 0.05 | 0.05 |
| | Dibutylhydroxytoluene | 0.005 | 0.005 | 0.005 | 0.005 | 0.005 |
| (E) | Polyoxyethylene hardened castor oil 60 | 0.5 | 0.3 | — | 0.4 | 0.05 |
| | Polysorbate 80 | 0.5 | 0.3 | 0.05 | — | 0.05 |
| Others | Tetrahydrozoline hydrochloride | 0.05 | — | 0.05 | 0.05 | 0.05 |
| | Neostigmine methylsulfate | 0.005 | — | 0.005 | 0.005 | 0.005 |
| | Chlorpheniramine maleate | 0.03 | 0.03 | 0.03 | 0.03 | 0.03 |
| | Pyridoxine hydrochloride | — | 0.05 | 0.05 | 0.05 | 0.05 |
| | Sodium hyaluronate | 0.02 | — | — | — | 0.02 |
| | Trometamol | — | 0.005 | — | — | 0.005 |
| | Boric acid | 1 | 1 | 1 | 1 | — |
| | Borax | 0.5 | 0.5 | 0.5 | 0.5 | 1 |
| | l-Menthol | 0.005 | — | — | — | 0.2 |
| | dl-Camphor | 0.002 | — | — | — | — |
| | d-Borneol | 0.003 | — | — | — | — |
| | Sodium edetate | 0.1 | 0.1 | 0.1 | 0.1 | 0.1 |

TABLE 7-continued

| Formulation | Example | | | | |
|---|---|---|---|---|---|
| (W/V %) | 34 | 35 | 36 | 37 | 38 |
| Potassium sorbate | — | — | — | — | 0.1 |
| Sodium chloride | 0.9 | 0.9 | 0.9 | 0.9 | 0.9 |
| Diluted hydrochloric acid/ sodium hydroxide (pH = 7) | Appropriate amount | | | | |
| Purified water | Balance | | | | |
| Total | 100 mL | | | | |
| (B) + (E) | 1.1 | 1.1 | 1.15 | 3.4 | 5.1 |
| Appearance stability | 5 | 5 | 5 | 5 | 5 |
| Dry eye improvement 1 | 5 | 5 | 5 | 5 | 5 |
| Dry eye improvement 2 | 7 | 7 | 7 | 7 | 7 |
| Eye irritation | 4 | 4 | 5 | 5 | 5 |

TABLE 8

| | Formulation | Example | | | | | |
|---|---|---|---|---|---|---|---|
| | (W/V %) | 39 | 40 | 41 | 42 | 43 | 44 |
| (A) | Retinol palmitate | 50,000 units | 50,000 units | 100,000 units | 100,000 units | 200,000 units | 200,000 units |
| (B) | Polyoxyethylene (200) polyoxypropylene glycol (70) *1 | 2 | 0.5 | — | — | — | — |
| | Polyoxyethylene (160) polyoxypropylene glycol (30) *2 | 0.3 | — | 3 | — | 5 | — |
| | Polyoxyethylene (54) polyoxypropylene glycol (39) *3 | — | 1 | — | 5 | — | 7.5 |
| (C) | Castor oil | 0.3 | 1 | 1 | 2 | — | — |
| | Soybean oil | — | — | — | — | — | — |
| | Sesame oil | — | — | — | — | — | 0.1 |
| | Peanut oil | — | — | — | — | 1 | — |
| | Purified lanolin | — | — | — | — | — | 0.1 |
| (D) | d-α-Tocopherol acetate | 0.05 | 0.05 | 0.1 | 1 | 0.05 | 0.05 |
| | Dibutylhydroxytoluene | 0.005 | 0.005 | 0.005 | 0.005 | 0.005 | 0.005 |
| (E) | Polyoxyethylene hardened castor oil 60 | — | 0.1 | 0.1 | — | 0.1 | — |
| | Polysorbate 80 | — | 0.05 | — | 0.1 | — | 0.2 |
| Others | Trometamol | — | 0.005 | — | 0.005 | 0.005 | — |
| | Boric acid | 1 | 1 | 1 | — | — | 1 |
| | Borax | 0.5 | 0.5 | 0.5 | 1 | 1 | 0.5 |
| | Sodium edetate | 0.1 | 0.1 | 0.1 | 0.1 | 0.1 | 0.1 |
| | Sodium chloride | 0.9 | 0.9 | 0.9 | 0.9 | 0.9 | 0.9 |
| | Diluted hydrochloric acid/ sodium hydroxide (pH = 7) | Appropriate amount | | | | | |
| | Purified water | Balance | | | | | |
| Total | | 100 mL | | | | | |
| (B) + (E) | | 2.3 | 1.65 | 3.1 | 5.1 | 5.1 | 7.7 |
| Appearance stability | | 4 | 5 | 5 | 5 | 5 | 5 |
| Dry eye improvement 1 | | 5 | 5 | 5 | 5 | 5 | 5 |
| Dry eye improvement 2 | | 7 | 7 | 7 | 7 | 7 | 7 |
| Eye irritation | | 5 | 5 | 5 | 5 | 5 | 5 |

As stated hereinabove, the ophthalmic compositions of the invention showed pronounced effects on dry eye symptoms (severity level: 4), particularly, on severe symptoms.

The starting materials used in the examples are indicated below.
* 1: Unilub 70DP-950B, JPE, made by NOF Corporation or Lutrol F127, JPE, made by BASF
* 2: Pronon #188P, JPE, made by NOF Corporation
* 3: Pronon #235P, JPE, made by NOF Corporation

The invention claimed is:
1. An ophthalmic composition comprising:
(A) 50,000 to 500,000 units/100 mL of vitamin A,
(B) 0.2 to 10 W/V % of a polyoxyethylene polyoxypropylene glycol selected from the group consisting of polyoxyethylene (200) polyoxypropylene (70) glycol, polyoxyethylene (160) polyoxypropylene (30) glycol, and polyoxyethylene (54) polyoxypropylene (39) glycol,
(C) 0.01 to 5 W/V % of an oil ingredient selected from the group consisting of castor oil, soybean oil, sesame oil, olive oil, almond oil, wheat germ oil, corn oil, canola oil, sunflower oil, and purified lanolin,
(D) 0.001 to 0.5 W/V % of vitamin E or dibutylhydroxytoluene,
(E) 0.001 to 1.0 W/V % of a polyoxyethylene hardened castor oil and/or a polyoxyethylene sorbitain fatty acid ester,
sodium edetate,
boric acid, and trometamol; and wherein a total content of the ingredients (B) and (E) is 1.1 to 20.001 W/V %; and wherein said composition contains no antiseptic selected from the group consisting of benzalkonium chloride, benzethonium chloride, sorbic acid or a salt thereof, paraoxybenzoic acid esters, chlorhexidine gluconate, thimerosal, phenyl ethyl alcohol, alkyldiaminoethylglycine hydrochloride, polyhexanide hydrochloride, and polydronium chloride.

2. The ophthalmic composition of claim 1, wherein the ingredient (A) is retinol palmitate, retinol acetate or retinoic acid.

3. The ophthalmic composition of claim 1, wherein said composition is the ophthalmic composition for contact lens.

4. The ophthalmic composition of claim 1, wherein ingredient (C) is castor oil.

5. A method for treating dry eye, which comprises the administration an ophthalmic composition according to claim 1.

6. The method of claim 5, wherein the ophthalmic composition is formulated with no antiseptic.

7. The method of claim 5, wherein the ingredient (A) is retinol palmitate, retinol acetate or retinoic acid.

8. The method of claim 5, wherein said composition is the ophthalmic composition for contact lens.

9. The method of claim 5, wherein ingredient (C) is castor oil.

10. An ophthalmic composition consisting of:

(A) 50,000 to 500,000 units/100 mL of vitamin A, (B) 0.2 to 10 W/V % of polyoxyethylene polyoxypropylene glycol selected from the group consisting of polyoxyethylene (200) polyoxypropylene (70) glycol, polyoxyethylene (160) polyoxypropylene (30) glycol, and polyoxyethylene (54) polyoxypropylene (39) glycol, (C) 0.01 to 5 W/V % of an oil ingredient selected from the group consisting of castor oil, soybean oil, sesame oil, peanut oil, olive oil, almond oil, wheat germ oil, corn oil, canola oil, sunflower oil and purified lanolin, (D) 0.001 to 0.5 W/V % of vitamin E or dibutylhydroxytoluene, (E) 0.001 to 1.0 W/V % of a polyoxyethylene hardened castor oil and/or a polyoxyethylene sorbitan fatty acid ester, sodium edetate, boric acid, trometamol, and optionally at least one selected from the group consisting of polyhydric alcohols, surfactants other than the ingredients (B) and (E), buffering agents, thickening agents, sugars, pH adjusters, tonicity agents, stabilizing agents, cooling agents, drugs, and water; and wherein a total content of the ingredients (B) and (E) is 1.1 to 20.001 W/V %, and wherein said composition contains no antiseptic selected from the group consisting of benzalkonium chloride, benzethonium chloride, sorbic acid or a salt thereof, paraoxybenzoic acid esters, chlorhexidine gluconate, thimerosal, phenyl ethyl alcohol, alkyldiaminoethylglycine hydrochloride, polyhexanide hydrochloride, and polydronium chloride.

* * * * *